United States Patent
Zeller

(10) Patent No.: US 10,295,613 B2
(45) Date of Patent: May 21, 2019

(54) METHOD AND APPARATUS FOR UPDATING MULTIPLE MAGNETIC RESONANCE DATASETS ACQUIRED USING A PARALLEL ACQUISITION TECHNIQUE

(71) Applicant: Siemens Healthcare GmbH, Erlangen (DE)

(72) Inventor: Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/720,495

(22) Filed: Sep. 29, 2017

(65) Prior Publication Data

US 2018/0095143 A1 Apr. 5, 2018

(30) Foreign Application Priority Data

Sep. 30, 2016 (DE) ........................ 10 2016 219 052

(51) Int. Cl.
*G01R 33/00* (2006.01)
*A61B 5/055* (2006.01)
(Continued)

(52) U.S. Cl.
CPC .......... *G01R 33/0023* (2013.01); *A61B 5/055* (2013.01); *G01R 33/20* (2013.01); *G01R 33/543* (2013.01); *G01R 33/5608* (2013.01); *G01R 33/5611* (2013.01); *G01R 33/4828* (2013.01); *G01R 33/50* (2013.01)

(58) Field of Classification Search
CPC .. G01R 33/0023; G01R 33/20; G01R 33/543; G01R 33/5608; G01R 33/5611; G01R 33/4828; G01R 33/50; A61B 5/055
See application file for complete search history.

(56) References Cited

U.S. PATENT DOCUMENTS 7,486,839 B2 *   2/2009   Moriguchi ........... G01R 33/285
                                              382/131
8,184,879 B2 *   5/2012   Geier .................... G01R 33/482
                                              324/309
(Continued)

OTHER PUBLICATIONS

Liu et al., "DWI Using Navigated Interleaved Multishot EPI with Realigned GRAPPA Reconstruction," Magnetic Resonance in Medicine, vol. 75, pp. 280-286 (2016).
(Continued)

*Primary Examiner* — Dixomara Vargas
(74) *Attorney, Agent, or Firm* — Schiff Hardin LLP

(57) ABSTRACT

In a method and magnetic resonance (MR) apparatus for creating a common updating kernel for at least two datasets, a first dataset is acquired from a subject that includes Nyquist undersampled measurement data acquired from at least two reception coils of an MR scanner, and that also includes calibration data. At least one further dataset is acquired, that contains Nyquist undersampled measurement data acquired with said coils, and also includes calibration data. A common calibration dataset is created from the calibration data in the first and the at least one further dataset. An updated first dataset and at least one updated further dataset are determined using the common calibration dataset. A combination image dataset can be produced from these updated datasets.

8 Claims, 4 Drawing Sheets

(51) Int. Cl.
   *G01R 33/20* (2006.01)
   *G01R 33/54* (2006.01)
   *G01R 33/56* (2006.01)
   *G01R 33/561* (2006.01)
   G01R 33/48 (2006.01)
   G01R 33/50 (2006.01)

(56) References Cited

U.S. PATENT DOCUMENTS

| | | | | |
|---|---|---|---|---|
| 8,570,034 | B2* | 10/2013 | Stemmer | G01R 33/246 324/307 |
| 8,699,773 | B2* | 4/2014 | Akcakaya | G06T 11/008 382/131 |
| 9,317,917 | B2* | 4/2016 | Stemmer | G06T 7/0012 |
| 9,366,740 | B2* | 6/2016 | Kecskemeti | G01R 33/5602 |
| 9,396,561 | B2* | 7/2016 | Dumoulin | G01R 33/5611 |
| 9,588,207 | B2* | 3/2017 | Weller | G01R 33/5611 |
| 9,649,393 | B2* | 5/2017 | Ahrens | A61K 49/10 |
| 9,655,522 | B2* | 5/2017 | Li | G06K 9/52 |
| 9,658,304 | B2* | 5/2017 | Lin | G01R 33/4818 |
| 2005/0058368 | A1* | 3/2005 | Moriguchi | G01R 33/285 382/280 |
| 2008/0024132 | A1 | 1/2008 | Brau et al. | |
| 2009/0092303 | A1 | 4/2009 | Griswold et al. | |
| 2014/0376794 | A1* | 12/2014 | Dumoulin | G01R 33/5611 382/131 |
| 2016/0041249 | A1 | 2/2016 | Lee et al. | |

OTHER PUBLICATIONS

Blaimer et al., "Comparison of Phase-Constrained Parallel MRI Approaches: Analogies and Differences," Magnetic Resonance in Medicine, pp. 1-4 (2015).

Blaimer et al., "Virtual Coil Concept for Improved Parallel MRI Employing Conjugate Symmetric Signals," Magnetic Resonance in Medicine, vol. 61, pp. 93-102 (2009).

* cited by examiner

METHOD AND APPARATUS FOR UPDATING MULTIPLE MAGNETIC RESONANCE DATASETS ACQUIRED USING A PARALLEL ACQUISITION TECHNIQUE

BACKGROUND OF THE INVENTION

Field of the Invention

The invention concerns updating multiple magnetic resonance datasets acquired using a parallel acquisition technique, in particular multiple magnetic resonance datasets acquired using a parallel acquisition, from which a combination image dataset is to be created.

Description of the Prior Art

Magnetic resonance (MR) technology (the abbreviation MR stands for magnetic resonance below) is a known modality with which images of the inside of an examination object can be generated. Expressed in simplified terms, the examination object is positioned in a magnetic resonance scanner in a strong, static, homogeneous basic magnetic field, also referred to as a B0 field, with field strengths of 0.2 Tesla up to 7 Tesla or more, so that nuclear spins of the object are oriented along the basic magnetic field. In order to trigger nuclear spin resonances, radio-frequency excitation pulses (RF pulses) are radiated into the examination object. The triggered nuclear spin resonances produce signals (MR signals) that are measured in the form of so-called k-space data, from which MR images are reconstructed or spectroscopic data are determined. For spatially coding the measurement data, rapidly switched magnetic gradient fields are superimposed on the basic magnetic field. The recorded measurement data are digitized and entered into a k-space matrix (memory) in the form of complex numerical values. An associated MR image can be reconstructed from the k-space matrix populated with such values, e.g. using a multidimensional Fourier transformation.

In an MR image, the magnitude of the MR signal (signal intensity) and the phase, i.e. the direction of the magnetization vector corresponding to the signal, exist for every image point.

There are many applications of magnetic resonance tomography in which it is desirable to distinguish between tissue types.

In the case of tissue types with a different chemical shift, a different magnetic field results at the nuclei of the respective tissues, leading to different resonant frequencies. This leads to different phase angles of the respective tissues (acting as signal sources) during acquisition of the MR signal. The most prominent examples of two differing tissue types in the magnetic resonance signal are fat and water, although other applications are also known. The resonant frequencies of fat and water differ from each other by approx. 3.3 ppm (parts per million). One way to separate the signals of two different tissue types, such as fat and water, is to make use of the phase information of acquired MR signals.

In this regard it is customary, in conventional methods for distinguishing between water-dominated and fat-dominated tissues, to capture two (or more) magnetic resonance signals for each image point. In methods of this type, for example two-point Dixon or three-point Dixon techniques, for each image point, at least one magnetic resonance signal in which a phase of the magnetic resonance signal of a water-containing tissue has the same phase as the phase of a magnetic resonance signal of a fat-containing tissue, and at least one magnetic resonance signal in which a phase of a magnetic resonance signal of the water-containing tissue has an opposite phase to the phase of the magnetic resonance signal of the fat-containing tissue, are acquired at different echo times. It is then possible, with the use of the acquired magnetic resonance signals for each image point, to distinguish between water-dominated and fat-dominated tissues. In this regard the image datasets acquired for each image point can be merged in to a combination image dataset, which represents only fat or only water.

Other acquisition techniques are known in which combination images are created from at least two acquired MR images, and differing tissues distinguished. These include, for example, methods for creating parameter maps for an examination object, e.g. T1, T2 or T2* mapping methods, with T1 giving a rate of a longitudinal relaxation of the magnetization, T2 a rate of a transverse relaxation of the magnetization, and T2* an effective rate of the free induction decay (FID), and e.g. proton density (PD) T2 methods.

For creating T2 and T2* maps, image datasets with varying echo time are best-suited. For creating T1 maps, the repetition time is changed between the at least two image datasets. The combination image dataset is obtained via an exponential fit in each case.

For this purpose, individual image datasets can be acquired one after another, respectively, in segmented form, or line-by-line, in k-space. The k-space lines belonging to an image dataset are assigned thereto, and determined from the image datasets of the combination image dataset.

For this purpose, multiple sequences are available for data acquisition. For example, both gradient echo-based and also spin echo-based sequences are known for acquisition of T1 maps. In the case of the Dixon technique, all sequences such as FLASH, spin echo or turbo spin echo, also referred to as RARE, can be used as long as two different echo times can be implemented.

Common to all these techniques is that at least two acquisition operations (at least two MR images) are implemented for each image point, e.g. at different echo times, in order to achieve different contrasts through processing of the acquired MR images. Consequently, the aforementioned techniques for distinguishing between differing tissues are also referred to as multi-contrast techniques.

Techniques called parallel acquisition techniques, such as GRAPPA ("GeneRalized Autocalibrating Partially Parallel Acquisition") or SENSE ("Sensitivity Encoding") are known, in which only one set of measurement data, under-sampled in k-space according to the Nyquist theorem, is acquired with the use of multiple RF coils, in order to shorten the total measuring time needed for acquisition of the measurement data, or to increase the resolution. In this regard the "missing" measurement data are updated (obtained or generated) from the measured measurement data on the basis of sensitivity data for the RF coils that are used and, in a sub-region of k-space actually to be sampled (filled with data) for the measurement, calibration data are sampled fully according to the Nyquist criterion.

If a parallel acquisition technique is employed in conjunction with a multi-contrast technique, then for each of the at least two acquisitions of the measurement data for the examination object, an individual set of calibration data is acquired, and missing measurement data are updated for in each case. An already improved method of this type, which uses parallel acquisition techniques with combination images generated from at least two parallel datasets, is described in US 2016/0041249 A1.

SUMMARY OF THE INVENTION

An object of the invention is to achieve an improved application of parallel acquisition techniques in connection with multi-contrast methods.

The inventive method for creating a common updating kernel for at least two magnetic resonance datasets acquired from an examination object has the following steps.

A first dataset is acquired from the examination object composed of measurement data acquired with at least two receiving coils that are Nyquist undersampled, with the measurement data acquired by the at least two receiving coils including calibration data.

At least one further dataset is acquired from the examination object, composed of measurement data acquired with at least two receiving coils that are Nyquist undersampled, with the measurement data of the further dataset acquired by the at least two receiving coils also including calibration data.

A common calibration dataset is created from the calibration data in the two acquired datasets.

An updated first dataset and updated further datasets are generated on the basis of the created common calibration dataset and on the basis of the first dataset and the further datasets.

The inventive creation of only one common calibration dataset makes it possible for all acquired datasets to be treated the same and in one pass. Furthermore, an inventive common calibration dataset enables a higher signal-to-noise ratio (SNR) in the datasets updated from the acquired datasets on the basis of the common calibration dataset, and also higher acceleration factors in the context of the parallel acquisition technique with which the datasets are acquired, even that technique is implemented only with a few reception channels (receiving coils). In this regard the creation of the common calibration dataset is easy to implement.

An inventive method for generating at least one combination image dataset for an examination object from a first dataset and at least one further dataset for the examination object, wherein the first data and the at least one further dataset each contain Nyquist undersampled measurement data acquired with at least two receiving coils, and calibration data, has the steps.

The first dataset and the at least one further dataset are provided to a computer.

A common calibration dataset for the acquired datasets is created in the computer described above.

An updated first dataset and updated further datasets are determined in the computer on the basis of the created common calibration dataset and on the basis of the first dataset and the further datasets.

At least one combination image dataset is crated in the computer from the updated first dataset and the updated further datasets and is provide from the computer as a datafile.

The inventive use of a common calibration dataset allows higher accelerations to be achieved during acquisition of the datasets with a parallel acquisition technique, as well as improving the SNR achieved through the updating, so that both the datasets updated on the basis of the common calibration dataset, and the combination image dataset created from the updated datasets, have a higher quality than when using individual calibration datasets.

An inventive magnetic resonance system has a scanner with a basic field magnet, a gradient coil arrangement, a radio-frequency antenna, and a control computer configured to implement the inventive method, with a radio-frequency transmit/receive controller and an updating processor.

The present invention also encompasses a non-transitory, computer-readable data storage medium encoded with programming instructions (program code) that, when the storage medium is loaded into a computer or computer system of a magnetic resonance apparatus, cause the computer or computer system to operate the magnetic resonance apparatus in order to implement any or all of the embodiments of the invention according to the invention, as described above.

The advantages and implementations specified with reference to the method apply as well to the magnetic resonance system and the electronically readable data storage medium.

DESCRIPTION OF THE PREFERRED EMBODIMENTS

Figure 1:
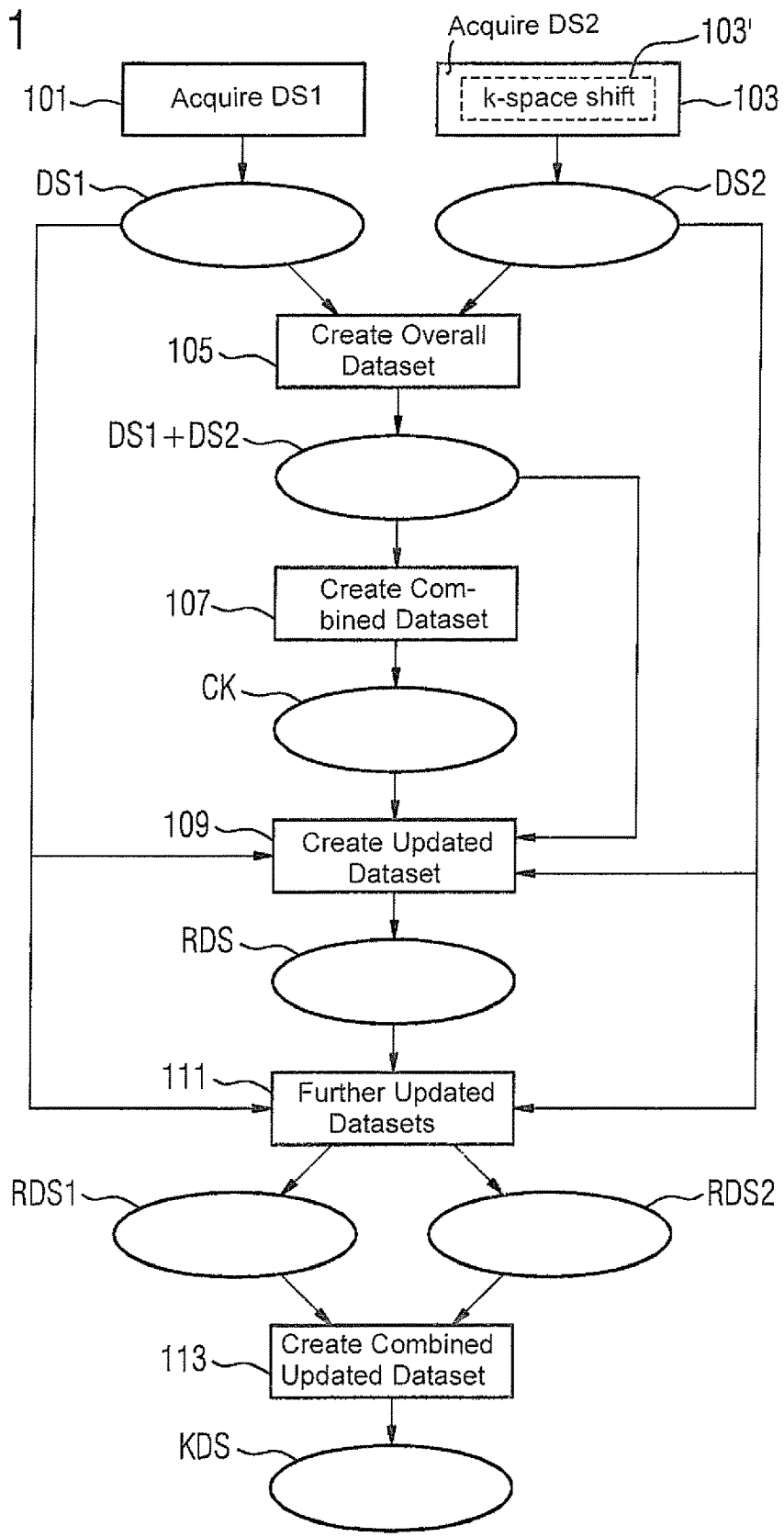
FIG. 1 is a flowchart of the inventive method.

FIG. 1 shows a flowchart of the inventive method for creating a common updating kernel for at least two datasets acquired from an examination object with the use of magnetic resonance, and a method for generating at least one combination image dataset (KDS) for an examination object from a first dataset and at least one further dataset.

A first dataset DS1 for the examination object is acquired (Block 101) and at least one further dataset DS2 for the examination object is acquired (Block 103). The first and also every further dataset DS1, DS2 contains Nyquist undersampled measurement data acquired with at least two receiving coils, and calibration data. The calibration data in datasets DS1, DS2 can also have been acquired in a separate step.

Figure 3:
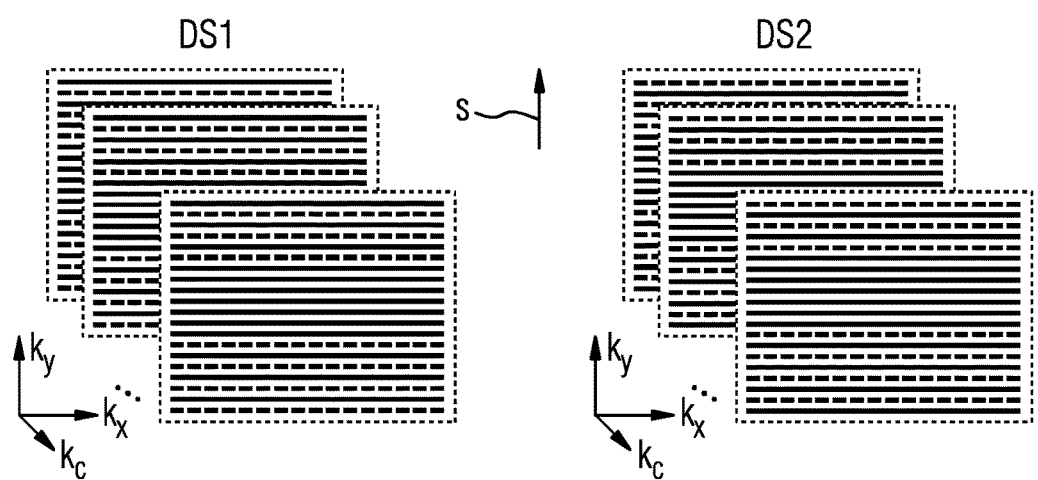
FIG. 3 shows an exemplary shift, in schematic form, of k-space data in a dataset to be acquired.

During the acquisition of the further dataset DS2, the acquired measurement data can be shifted in k-space according to a predetermined shift, compared with measurement data acquired in the first dataset DS1 (Block 103'). This is shown as an example in FIG. 3, in which an exemplary first dataset DS1 is shown on the left, in which the acquired measurement data are distributed in a specific manner. In the further dataset DS2 represented in FIG. 3, this distribution of the acquired measurement data is shifted by a shift s, being an upward shift in the case represented. A shift of this type leads to an additional linear phase in the image domain, which leads to an additional spatial variation in the coil sensitivities. As a result, the quality achievable during an updating of the undersampled dataset is improved because this increases with the spatial variation of the coil sensitivities. If the shift s is chosen such that the distribution is shifted by one k-space line, for example a shift of FOV/2 is produced in the image domain with the result that a maximum separation, and therefore easier differentiation of two simultaneously measured layers, is achieved in the image domain.

Figure 2:
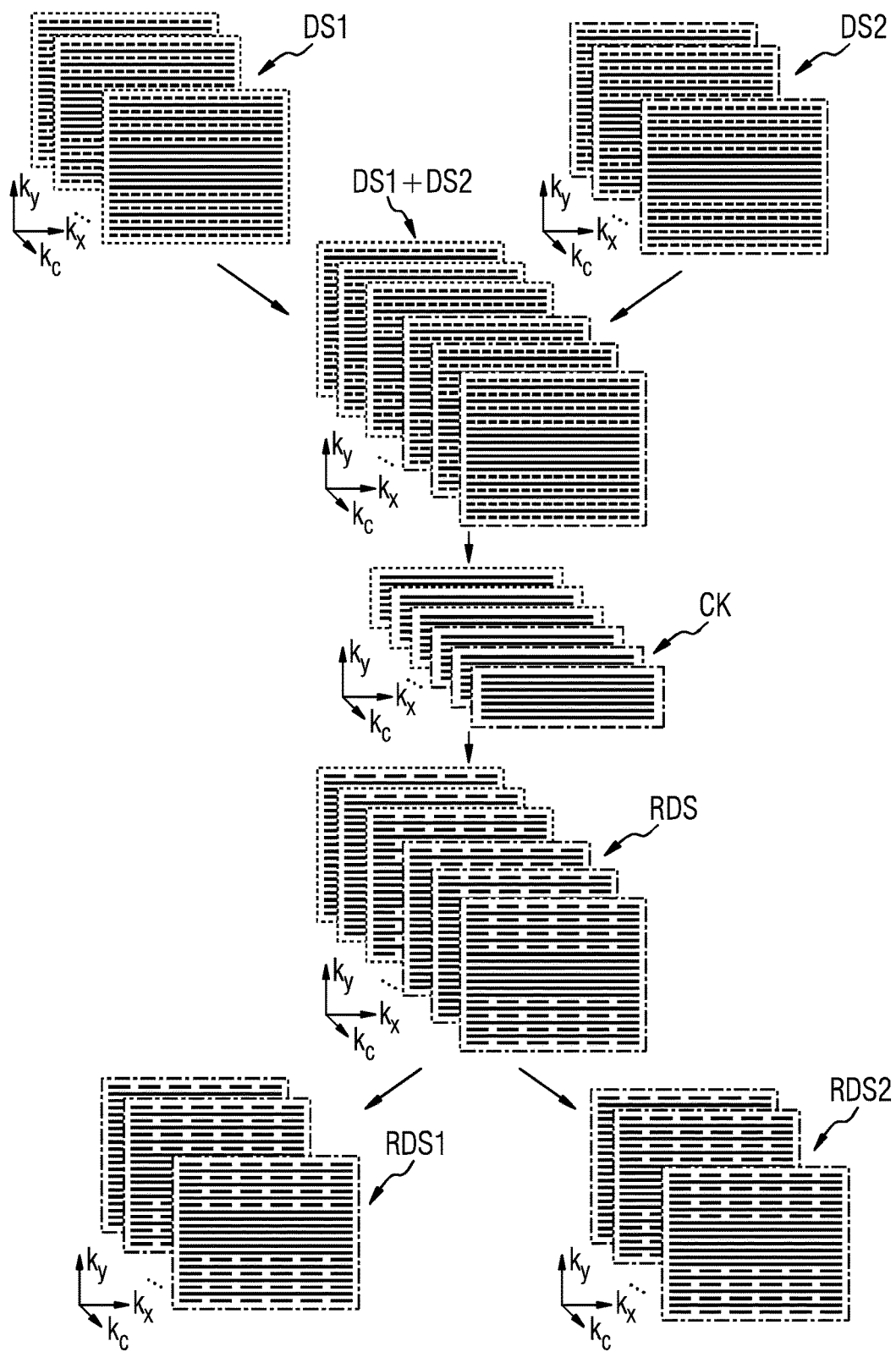
FIG. 2 shows examples, in schematic form, of datasets acquired and generated in the inventive method for further illustration of the sequence of the inventive method.

This is illustrated further in FIG. 2 in which, in schematic form, a first dataset DS1 and a further dataset DS2 are represented, which contain measurement data acquired by multiple receiving coils. For easier differentiation and assignment, the measurement data acquired by a receiving coil and contained in the first dataset DS1 are framed with a dotted line, whereas the measurement data acquired by a receiving coil and contained in the represented further dataset DS2 are framed with a dot-dash line.

The acquired measurement data are represented in FIG. 2 in the form of measurement data acquired along k-space lines in the $k_x$–$k_y$ plane in k-space, the measurement data acquired with differing receiving coils being distinguished in the dimension $k_c$. The principle underlying the invention can also be applied to other acquisition trajectories in k-space. For simplifying the representation, a line-by-line sampling is shown in each case in FIGS. 2 and 3, although this is not to be considered as a restriction.

As is represented, not all k-space lines are acquired in the first dataset DS1, nor in the further dataset DS2, but instead only an undersampled quantity of measurement points are filled, corresponding to the acceleration factor that is used in the parallel acquisition. In the representation, as an example, the k-space lines shown with a solid line are actually acquired (filled) k-space lines; the k-space lines shown with short dashes were not acquired so that in total one undersampled first dataset DS1 and also one undersampled further dataset DS2 are acquired for each receiving coil ($k_c$). In one region of k-space, however, such as in a central region, complete calibration data according to the Nyquist theorem are acquired in each case, as is represented by those regions each being shown with every k-space line acquired (solid lines). The measurement data acquired with the respective receiving coils therefore include calibration data.

From calibration data contained in the acquired datasets (DS1, DS2), a common calibration dataset CK is created (Block 107). To this end an overall dataset DS1+DS2 can first be created (Block 105), which contains all the data of all acquired datasets DS1, DS2, and from which the calibration data contained in each case are taken and combined into the common calibration dataset CK. Measurement data acquired by the same receiving coils, but which are to be assigned to differing acquired datasets DS1, DS2, have an individual coordinate in the "coil dimension" $k_c$ in each case. It is also possible for only the calibration data to be extracted directly from the acquired datasets DS1, DS2 and combined into the common calibration dataset CK.

During the creation of the common calibration dataset CK, calibration data of the first dataset DS1 can be taken into account according to the at least two receiving coils, and calibration data from further acquired datasets DS2 can be taken into account virtually as calibration data from further receiving coils, so that the common calibration dataset CK is larger, corresponding to the acquired further datasets DS2, in the direction of the "coil dimension" $k_c$ (twice as large in the case of a further dataset DS2), than an acquired dataset DS1, DS2. The calibration data from further datasets are therefore taken into account in the common calibration dataset as so-called virtual receiving coils. The introduction of virtual receiving coils of this type can be easily incorporated into an existing implementation of parallel acquisition techniques since existing structures can be used almost unchanged and just a different grouping of the calibration data is used.

On the basis of the created common calibration dataset CK and on the basis of the first (undersampled) dataset DS1 and the further (undersampled) datasets DS2, an updated first dataset RDS1 and updated further datasets RDS2 are determined (Block 111). In this regard, an updated dataset RDS can also first be created on the basis of all acquired measurement data of the first dataset DS1 and of the acquired further datasets DS2, or on the basis of the overall dataset DS1+DS2, and also on the basis of the common calibration dataset CK in each case (Block 109), from which the updated first dataset RDS1 and updated further datasets RDS2 are separated (Block 111).

The determination of the updated first dataset RDS1 and the updated further datasets RDS2 can be an updating of the acquired datasets DS1, DS2 on the basis of the created common calibration dataset CK in to an updated dataset RDS, and a separation of an updated first dataset RDS1 and updated further datasets RDS2 out of the updated dataset RDS.

A separation of this type, of the updated dataset RDS in to the first updated dataset RDS1 and the further datasets RDS2 can be effected, for example, on the basis of receiving coils assigned to the common calibration dataset KDS, i.e. according to an assigned "coordinate" in the "coil dimension" $k_c$.

This is illustrated again FIG. 2. In the represented updated overall dataset RDS and the updated first dataset RDS1, and the represented updated further dataset RDS2, updated measurement data is represented in the form of k-space lines shown with long lines.

The first acquired dataset DS1 and the further acquired datasets DS2 can be datasets from which a combination image dataset KDS is to be created.

Consideration is given to the first acquired dataset DS1 and the further acquired datasets DS2 being acquired according to a Dixon method or according to a method for creating parameter maps, e.g. T1, T2, or T2* maps, in order to be able to create corresponding combination image datasets in each case, e.g. for representing only one spin species or the aforementioned parameters.

In this case, a combination image KDS can be created from the updated first dataset RDS1 and the updated further datasets RDS2 (Block 113).

Thus an implementation of the method described above, at least according to Blocks 101, 103, 107, 111, and 113 described above, makes it possible to implement a method for generating at least one combination image dataset KDS for an examination object from a first and at least one further dataset DS1, DS2 for the examination object, wherein the first and the at least one further dataset DS1, DS2 contain Nyquist undersampled measurement data respectively acquired with at least two receiving coils, and wherein the measurement data acquired by the at least two receiving coils include calibration data.

Figure 4:
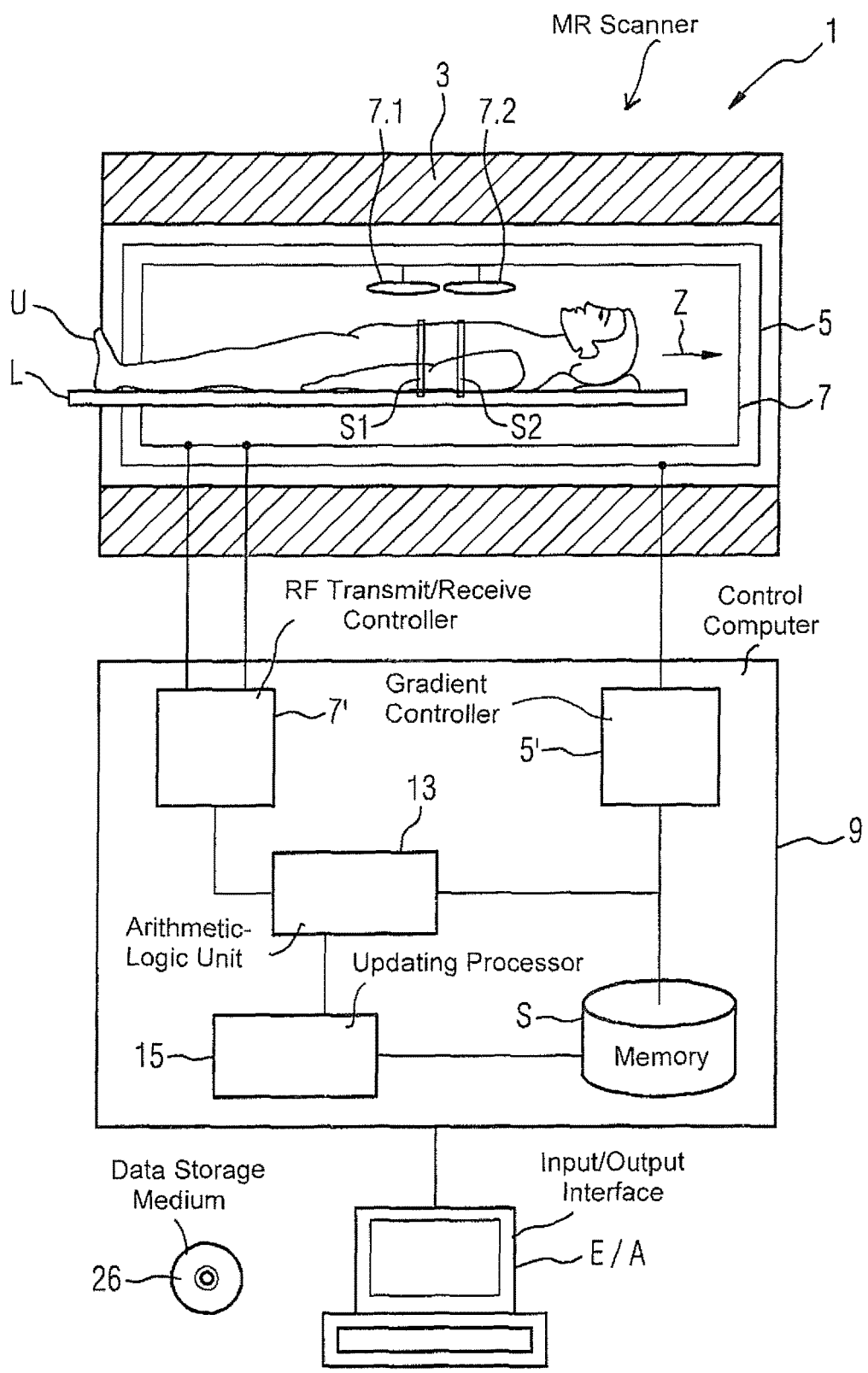
FIG. 4 schematically illustrates an inventive magnetic resonance apparatus.

FIG. 4 represents, in schematic form, an inventive magnetic resonance apparatus that has a scanner 1. The scanner 1 has a basic field magnet 3 that generates the basic magnetic field, a gradient coil arrangement 5 that generates the gradient fields, a radio-frequency antenna 7 that radiates and receives radio-frequency signals, and a control computer 9 configured to implement the inventive method. In FIG. 4 these sub-units of the magnetic resonance scanner 1 are only represented in schematic form. The radio-frequency antenna 7 can be formed of multiple subsidiary units, in particular at least two coils like the coils 7.1 and 7.2 shown in schematic form, which can be configured either to only transmit radio-frequency signals or to only receive the triggered radio-frequency signals, or to do both.

To examine an examination object U, for example a patient or a phantom, this is introduced on a table L in to the magnetic resonance scanner 1, in to its measuring volume. The slices S1 and S2 represent, as examples, two different slices of the examination object that can be detected simultaneously during an acquisition of MR signals.

The control computer 9 controls the magnetic resonance system, and in particular controls the gradient coil arrangement 5 via a gradient controller 5' and the radio-frequency antenna 7 via a radio-frequency transmit/receive controller 7'. In this regard the radio-frequency antenna 7 can have multiple channels in which signals can be individually transmitted or received.

The radio-frequency antenna 7, together with its radio-frequency transmit/receive control controller 7', is responsible for generating and radiating (transmitting) a radio-frequency alternating field for manipulating the nuclear spins in a region to be examined (in particular in slices S1 and S2) of the examination object U. The center frequency of the radio-frequency alternating field, also referred to as a B1 field, must be close to the resonant frequency of the spins to be manipulated. To generate the B1 field, currents controlled by the radio-frequency transmit/receive controller 7' in the radio-frequency antenna 7 are applied to the RF coils.

Furthermore the control computer 9 has an updating processor 15 that creates common updating kernels and reconstructs image data, and is configured so as to implement the inventive method for optimized acquisition of measurement data.

An arithmetic-logic unit 13 of the control computer 9 is configured so as to carry out all the computing operations needed for the necessary measurements and determinations. Intermediate results and results needed to this end or determined in this regard can be stored in a memory S of the control computer 9. The units represented need not necessarily be physically separate units, but instead just represent a breakdown into functional units, which can also be realized in fewer units or in just one individual physical unit.

Via an input/output interface E/A of the magnetic resonance apparatus, control commands can be entered by a user into the magnetic resonance apparatus and/or results can be displayed, such as image data.

An electronically readable data storage medium 26 is encoded with programming instructions (program code) that, when the storage medium 26 is loaded into the control computer 9, cause the control computer 9 to operate the magnetic resonance apparatus in order to implement any or all of the embodiments of the method as described above.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for creating a common updating kernel for at least two magnetic resonance (MR) datasets acquired from a subject, said method comprising:
   operating an MR data acquisition scanner to acquire a first dataset from a subject, said first dataset comprising Nyquist undersampled MR measurement data, acquired with at least two reception coils of said scanner, said MR measurement data of said first dataset comprising first calibration data;
   operating said MR data acquisition scanner to acquire at least one further dataset from said subject, said further dataset comprising Nyquist undersampled MR measurement data acquired with said at least two reception coils, and said MR measurement data in said at least one further dataset comprising second calibration data;
   providing said first and second datasets to a computer and, in said computer, generating a common calibration dataset from said first and second calibration data; and
   in said computer, producing an updated first image dataset and at least one updated further image dataset from said common calibration dataset and said first dataset and said at least one further dataset, and making the updated first and further image datasets available from said computer as a datafile for display thereof.

2. A method as claimed in claim 1 comprising generating said common calibration dataset by using said first calibration data as calibration data acquired by two reception coils among said at least two reception coils, and using said second calibration data as calibration data virtually acquired by further reception coils, other than said two reception coils, among said at least two reception coils.

3. A method as claimed in claim 1 comprising producing said updated first dataset and said at least one updated further dataset by first generating an updated dataset using said common calibration dataset, and then separating said updated first dataset and said updated at least further dataset from said updated dataset.

4. A method as claimed in claim 3 comprising separating said updated dataset into said first updated dataset and said at least one further updated dataset based on reception coils, among said at least two reception coils, assigned to said common calibration dataset.

5. A method as claimed in claim 1 comprising acquiring the measurement data in said at least one further dataset shifted in k-space according to a predetermined shift, compared with the measurement data acquired in said first dataset.

6. A method as claimed in claim 1 comprising acquiring said first dataset and said at least one further dataset by operating said MR data acquisition scanner according to a Dixon method, or according to a method for creating parameter maps.

7. A magnetic resonance (MR) apparatus comprising:
   an MR data acquisition scanner;
   a computer configured to operate said MR data acquisition scanner to acquire a first dataset from a subject, said first dataset comprising Nyquist undersampled MR measurement data, acquired with at least two reception coils of said scanner, said MR measurement data of said first dataset comprising first calibration data;
   said computer being configured to operate said MR data acquisition scanner to acquire at least one further dataset from said subject, said further dataset comprising Nyquist undersampled MR measurement data acquired with said at least two reception coils, and said MR measurement data in said at least one further dataset comprising second calibration data;
   said computer being configured to generate a common calibration dataset from said first and second calibration data; and
   said computer being configured to produce an updated first image dataset and at least one updated further image dataset from said common calibration dataset and said first dataset and said at least one further dataset, and to make the updated first and further image datasets available from said computer as a datafile for display thereof.

8. A non-transitory, computer-readable data storage medium encoded with programming instructions, said storage medium being loaded into a computer system of a magnetic resonance (MR) apparatus comprising an MR data acquisition scanner, and said programming instructions causing said computer system to:

receive a first dataset acquired from a subject, said first dataset comprising Nyquist undersampled MR measurement data, acquired with at least two reception coils of said scanner, said MR measurement data of said first dataset comprising first calibration data;

receive at least one further dataset acquired from said subject, said further dataset comprising Nyquist undersampled MR measurement data acquired with said at least two reception coils, and said MR measurement data in said at least one further dataset comprising second calibration data;

generate a common calibration dataset from said first and second calibration data; and produce an updated first dataset and at least one updated further image dataset from said common calibration image dataset and said first dataset and said at least one further dataset, and make the updated first and further image datasets available from said computer as a datafile for display thereof.

\* \* \* \* \*